US012626823B2

(12) United States Patent
Jin et al.

(10) Patent No.: US 12,626,823 B2
(45) Date of Patent: May 12, 2026

(54) MEDICAL AND HEALTHCARE SERVICE PLATFORMS AND USES THEREOF

(71) Applicants: Rutgers, The State University of New Jersey, New Brunswick, NJ (US); Digital Health China Technologies, Co., Ltd., Beijing (CN)

(72) Inventors: Jing Jin, Basking Ridge, NJ (US); Wenzhao Shi, Beijing (CN); Anjiang Chen, Piscataway, NJ (US); Juan Xu, Beijing (CN); Yi Ge, Piscataway, NJ (US); Zheng Xu, Beijing (CN)

(73) Assignees: RUTGERS, THE STATE UNIVERSITY OF NEW JERSEY, New Brunswick, NJ (US); DIGITAL HEALTH CHINA TECHNOLOGIES, CO., LTD., Beijing (CN)

( * ) Notice: Subject to any disclaimer, the term of this patent is extended or adjusted under 35 U.S.C. 154(b) by 227 days.

(21) Appl. No.: 18/312,434

(22) Filed: May 4, 2023

(65) Prior Publication Data

US 2023/0360802 A1 Nov. 9, 2023

(30) Foreign Application Priority Data

May 5, 2022 (CN) .......................... 202210482706.0

(51) Int. Cl.
*G16H 50/50* (2018.01)
*G16H 80/00* (2018.01)

(52) U.S. Cl.
CPC ............. *G16H 50/50* (2018.01); *G16H 80/00* (2018.01)

(58) Field of Classification Search
CPC ........ G16H 50/50; G16H 80/00; G16H 20/00; G16H 50/20; G16H 40/67; G16H 50/70; G16H 50/30
See application file for complete search history.

(56) References Cited

U.S. PATENT DOCUMENTS

| | | | |
|---|---|---|---|
| 8,838,217 B2 | 9/2014 | Myr | |
| RE46,092 E | 8/2016 | Redlich | |
| 10,438,170 B2 | 10/2019 | Kozloski et al. | |
| 11,202,570 B2 | 12/2021 | Shelton, IV et al. | |
| 2008/0015418 A1* | 1/2008 | Jarrell | G16H 70/20 |
| | | | 600/300 |
| 2008/0228580 A1 | 9/2008 | Korman et al. | |
| 2014/0180780 A1 | 6/2014 | Stewart et al. | |
| 2015/0088546 A1 | 3/2015 | Balram et al. | |
| 2017/0068785 A1 | 3/2017 | Experton et al. | |

(Continued)

OTHER PUBLICATIONS

Li, W., Wu, Wj., Wang, Hm. et al. Crowd intelligence in AI 2.0 era. Frontiers Inf Technol Electronic Eng 18, 15â43 (2017). https://doi. org/10.1631/FITEE.1601859.*

(Continued)

*Primary Examiner* — Joshua B Blanchette
(74) *Attorney, Agent, or Firm* — FOX ROTHSCHILD LLP

(57) ABSTRACT

This disclosure provides a medical and healthcare service platform that is supported by a digital data currency system and provides medical and healthcare data processing, analyzing, and predicting based on a digital human system by integrating participating parties comprising individual persons, researchers, healthcare providers, and regulatory and public sectors.

18 Claims, 7 Drawing Sheets

(56) References Cited

U.S. PATENT DOCUMENTS

| | | | |
|---|---|---|---|
| 2018/0165588 A1 | 6/2018 | Saxena et al. | |
| 2018/0247191 A1 | 8/2018 | Katz et al. | |
| 2019/0005200 A1 | 1/2019 | Zimmerman et al. | |
| 2019/0087544 A1 | 3/2019 | Peterson | |
| 2019/0188627 A1 | 6/2019 | Hein et al. | |
| 2020/0097951 A1 | 3/2020 | Abramson et al. | |
| 2020/0218940 A1 | 7/2020 | Anglin et al. | |
| 2020/0303047 A1 | 9/2020 | Bostic et al. | |
| 2020/0311755 A1 | 10/2020 | Postrel | |
| 2021/0125732 A1* | 4/2021 | Patel ..................... | G06N 3/096 |
| 2021/0202107 A1 | 7/2021 | Bostic et al. | |
| 2022/0076841 A1* | 3/2022 | Abu El Ata ........... | G16H 50/30 |

OTHER PUBLICATIONS

B. R. Barricelli, E. Casiraghi and D. Fogli, "A Survey on Digital Twin: Definitions, Characteristics, Applications, and Design Implications," in IEEE Access, vol. 7, pp. 167653-167671, 2019, doi: 10.1109/ACCESS.2019.2953499.*

* cited by examiner

MEDICAL AND HEALTHCARE SERVICE PLATFORMS AND USES THEREOF

CROSS-REFERENCE TO RELATED APPLICATIONS

This application claims priority to Chinese Patent Application No. 202210-182706.0, filed May 5, 2022. The foregoing application is incorporated by reference herein in its entirety.

FIELD

The present invention relate generally to a medical and healthcare service platform and uses thereof.

BACKGROUND

With the development and progress of medical science and technology, there is an improved understanding of harms of illness to the body in real time and the impacts of various diseases on the body. As a result, people pay more attention to physical health. To better assist medical staff in the treatment of patients and promote the early recovery of patients, it is necessary to develop an efficient, convenient, and accurate medical service platform.

SUMMARY

This disclosure provides a medical and healthcare service platform that is supported by a digital data currency system and provides medical and healthcare data processing, analyzing, and predicting based on a digital human system by integrating participating parties comprising individual persons, researchers, healthcare providers, and regulatory and public sectors.

In some embodiments, the medical and healthcare service platform comprises: (i) a digital human replica system that constructs a digital human replica to provide virtual representation, modeling, and visualization services based on present and past medical and health data of physical persons; (ii) a digital human simuli system that constructs a digital human simuli to provide virtual simulation and modeling of future health and physiological evolution of a physical person based on the present and past medical and health data; (iii) a digital human agent system that represents virtual medical and health service professionals with specialties and functions, wherein the virtual medical and healthcare service professionals are formed based on professional knowledge and capabilities, specialties, and experiences of physical medical and healthcare professionals and characteristics and specialties of non-medical and healthcare professionals or practitioners; (iv) a digital human data acquisition system that collects biometric identification and medical related data, and (v) a digital data currency system that awards data sharing and contributions in a full ecosystem of data generation comprising data processing, data cleaning and denoising, data encryption and anonymization, data labeling and calibration, and data analytics, data contributions related to medical and healthcare services; and services provided by medical and healthcare professionals from clinical practices, drug companies from laboratories or clinical trial data, and academic researchers from research work.

In some embodiments, the digital human replica system receives input data from the human data acquisition system for both a target physical person and other persons with similar biomedical, social-demographical, occupational, and lifestyle characteristics for building, calibrating, and customizing the digital human simuli system for the target physical person to simulate the growing and aging, disease events, injury events, and their reactions to medicines and treatment plans.

In some embodiments, the digital human agent system creates a special digital human replica of actions, treatment plans, and decision makings of medical and healthcare professionals. In some embodiments, the digital human agent system is configured to execute simulated medical, care, and health services as an intervention based on simulation in a digital human simuli model of the digital human simuli system, In some embodiments, the digital human stimuli and the digital human agent system are integrated to perform model optimization to select and determine an optimal treatment or support plan to achieve an optimal health and medical outcome.

In some embodiments, the digital human digital data currency system awards digital currency for data contribution by the participating parties who interface with the digital human data acquisition system and wherein the data contribution results in improvement of performance of the digital human simuli system and the digital human agent system.

In some embodiments, the digital human replica system provides a representation of physical human bodies, and wherein the representation comprises one or more of: 3D contour body model, multi-dimensional anatomical model, multi-dimensional data feature tensor, and spatiotemporal transformation of health and disease state.

In some embodiments, the representation further comprises one or more of medical diagnosis and treatment; pharmaceutical use state quantity; diet, living and healthcare habits state quantity; environmental impact state quantity; virtual detection monitoring and observation modeling; and a process of psychophysiological changes for a full life cycle.

In some embodiments, the digital human replica system comprises a full retrospective system generated based on spatiotemporal data. In some embodiments, the spatiotemporal data comprises: retrospective of life cycle, retrospective of life course and event process, or retrospective of disease and psychophysiological social environment impact events.

In some embodiments, the digital human replica system provides virtual representation, modeling, and visualization service for both participant users and non-participant users of the medical and healthcare service platform. In some embodiments, the non-participant users have similar biomedical, social-demographical, occupational, and lifestyle characteristics to the participant users, and wherein the digital human replica system uses the characteristics of the non-participant users to infer and interpolate missing data of the participant users.

In some embodiments, the digital human replica system is configured to: identify the participant users using customizable identity and biometric information, or receive feedback on physical human health or medical processes.

In some embodiments, the non-participant users are identified by de-identified information created by: age groups, gender, or biometric group characteristics.

In some embodiments, the digital human simuli system comprises an organ or part simulation subsystem that simulates a change process by using organs or parts of a constructed digital human replica.

In some embodiments, the digital human simuli system comprises a simulation process dynamic visualization subsystem for dynamically visualizing changed data.

In some embodiments, the digital human agent system, through one or more deep neural network models, performs training and learning based on input data comprising: real-world doctors' treatment and prescription strategies, nursing and service strategies for nurses, therapists, research, experimentation, or development strategies for researchers, regulations and services for government agencies, wherein the digital human agent system generates digital human simuli models based on the input data, and wherein the digital human simuli models interact with a baseline digital human replica model.

In some embodiments, the digital human agent system creates deep neural network models of:

(a) doctors, nurses, or therapists to treat the digital human simuli and provide virtual instructions and services to physical persons on their healthcare and disease treatment process;

(b) researchers and experimental groups to conduct virtual tests and surveys on the digital human replica and the digital human simuli to conduct research and development of new medical devices, drugs, treatment plans, or general health and behavioral studies;

(c) health insurance providers that interact with the digital human replica about coverage and billing costs, insurance claims for ongoing treatments and services, and different treatment plans and insurance coverage and billing options;

(d) governing bodies, regulators, and digital security agencies to oversee, monitor and enforce critical health, medical, privacy protection, data security policy and regulations, freedom of information and disinformation suppression in virtual worlds;

(e) public health workers and platform users to provide related government services comprising medical material distribution, medical forms, and insurance claims; or (f) professionals who supervise scientific research and production services, and self-diagnosis services and volunteers who provide health diagnosis and treatment services to family members and family communities, wherein the digital human agent system undertakes medical treatment and care services, virtual simulation and modeling application.

In some embodiments, the present and past medical and health data comprises: real time data, events data, and historical data and paper records.

In some embodiments, the data acquisition system comprises an interface interacting with users and contributors of the medical and healthcare service platform to facilitate biomedical, healthcare, data inputs and labeling, and wherein the interface comprises one or more of: an interface for regular individual participants, an interface for doctors and hospitals, an interface for companies and R&D groups, or an interface to interact with datasets and data feeds provided by public agencies.

In some embodiments, the interface comprises: a wearable body health sensor interface, a digital human body multimodal data interface, or a digital human body medical record conversion interface.

In some embodiments, the medical and health data are acquired from: wearable sensors, medical records, or lab tests.

In some embodiments, the data acquisition system is configured to: clean collected data; perform desensitization processing on collected data; perform data privacy protection processing on the collected data; or visualize the collected data.

In some embodiments, the medical and healthcare service platform constructs a spatial-temporal virtual world that simulates external factors related to human health, disease, conditions, and wherein the external factors comprise one or more of: social activity, travel behavior, family environment, hospital, occupation, workplace, transportation, community, and city.

In some embodiments, the medical and healthcare service platform further comprises an auxiliary and interactive system interfacing between the virtual world of digital humans and real-world personal healthcare and government public health management to perform one or more of: auxiliary diagnosis and treatment, health care, nursing care, public health management, and smart device and robot interaction.

In some embodiments, the auxiliary diagnosis and treatment, health care, and nursing care comprises: real-world medical diagnosis and treatment; emergency responses; diagnosis and treatment of rare diseases; offline personal health care; family daily care, emotional care, or psychological counseling; real-world offline community health management services; or medical resource retrieval, distribution and sharing, equalization and fairness services.

In some embodiments, the public health management: conducts real-world government regulation, control disease, or infectious disease control; conducts national health education; prevents quack doctors or false medical information; or prevents and reduces major injury events with high accident rate and low rescue success rate.

In some embodiments, the medical and healthcare service platform comprises a hybrid data warehouse system for storing the medical and health data, wherein the hybrid data warehouse system comprises: a centralized data warehouse and a federated data warehouse, wherein the centralized data warehouse has an upload interface for users to upload their healthcare and medical data directly to the medical and healthcare service platform, and wherein the federated data warehouse has an application interface for the participating parties to share converted aggregate data and models from protected data sources within each party.

In some embodiments, the digital data currency system awards digital currency for one or more of: contributors based on entire data contribution and generation life cycles, contributions to early detection, tracking, and prevention of infectious diseases, success rate, and positive user feedback for healthcare worker agents, and successful applications and adoptions for research and discovery results from research and discovery agents.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combinations of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

The advantages and aspects of this disclosure will become more apparent when taken in conjunction with the accompanying figures and with reference to the following detailed description. Throughout the figures, the same or similar reference numbers refer to the same or similar elements.

DETAILED DESCRIPTION

Figure 1:
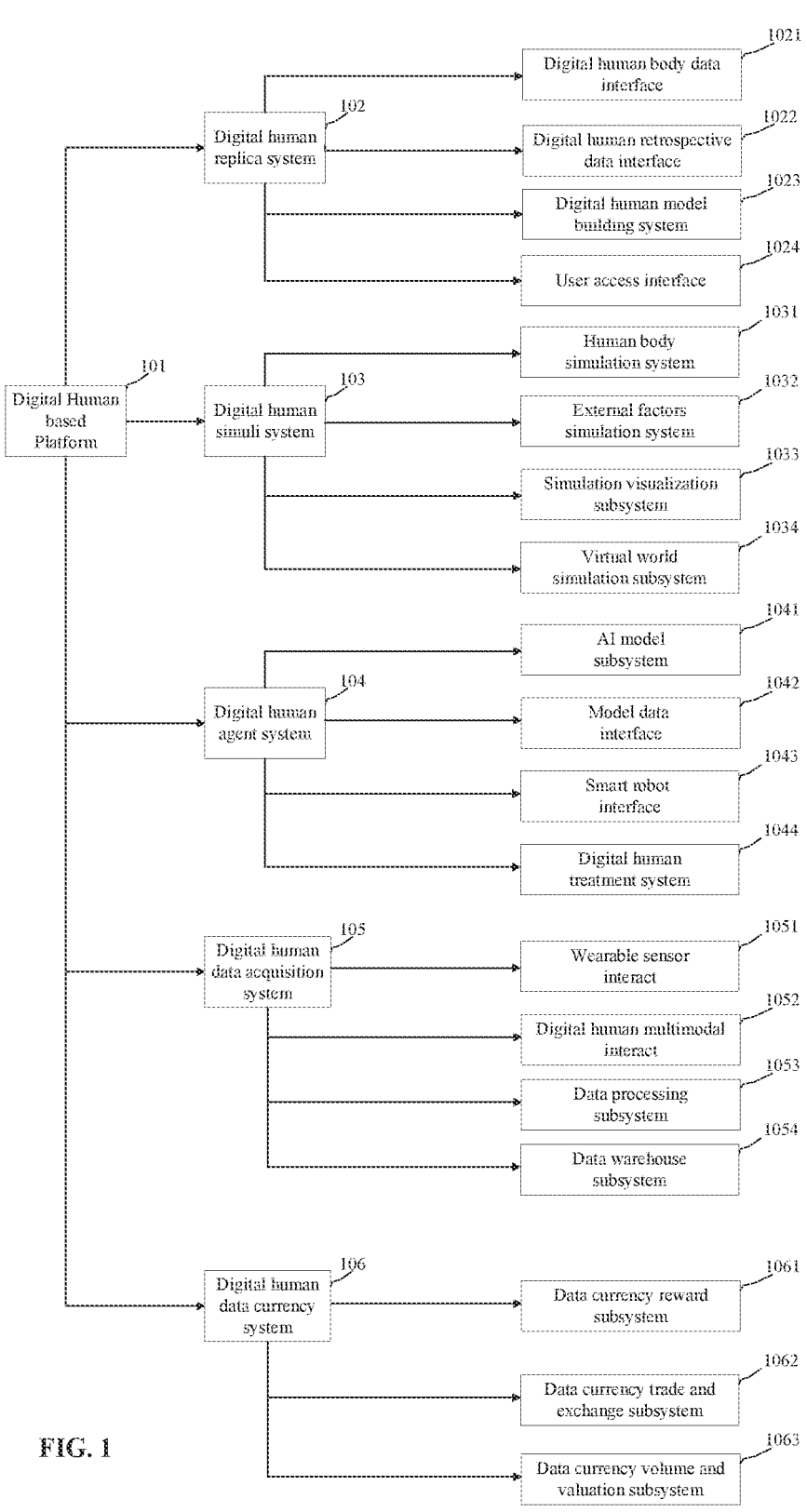
FIG. 1 illustrates an example medical and healthcare service platform based on a digital human system.

This disclosure provides a novel medical and healthcare service platform, method, and apparatus based on a human digital twin model. In some embodiments, the disclosed medical and healthcare service platform is supported by a digital data currency system and provides medical and healthcare data processing, analyzing, and predicting based on a digital human system by integrating participating parties comprising individual persons, researchers, healthcare providers, and regulatory and public sectors.

The disclosed medical and healthcare service platform, method, and apparatus have at least the following benefits. First, it allows users to readily understand their own health conditions. It is also beneficial for medical staff to understand the patient's physical health and the prediction of the severity of the disease. Second, it eliminates the limitations of the data collection time stage and the range of the collected data by fully considering various circumstances and incentives. Third, the collected data is desensitized and cleaned to ensure high accuracy of the data obtained from the simulation process of the human digital twin model and to closely conforms to the actual situation. Fourth, data privacy protection is performed on the collected data to avoid leakage of personally identifiable information and protect user data privacy. Fifth, it provides dynamic visualization of the simulation process that is helpful for medical staff or users to grasp the changing trend at any time. Sixth, the disclosed medical and healthcare service platform is also helpful for reconstructing a healthy medical service robot terminal. Furthermore, the disclosed medical and healthcare service platform can be implemented for various applications other than medical services, such as career development and the insurance industry.

In some embodiments, the medical and healthcare service platform may include:

(i) a digital human replica system that constructs a digital human replica to provide virtual representation, mod-eling, and visualization services based on present and past medical and health data of physical persons;

(ii) a digital human simuli system that constructs a digital human simuli to provide virtual simulation and modeling of future health and physiological evolution of a physical person based on the present and past medical and health data;

(iii) a digital human agent system that represents virtual medical and health service professionals with specialties and functions, wherein the virtual medical and healthcare service professionals are formed based on professional knowledge and capabilities, specialties, and experiences of physical medical and healthcare professionals and characteristics and specialties of non-medical and healthcare professionals or practitioners;

(iv) a digital human data acquisition system that collects biometric identification and medical-related data, and (v) a digital data currency system that awards data sharing and contributions in a full ecosystem of data generation comprising data processing, data cleaning and denoising, data encryption and anonymization, data labeling and calibration, and data analytics, data contributions related to medical and healthcare services; and services provided by medical and healthcare professionals from clinical practices, drug companies from laboratories or clinical trial data, and academic researchers from research work.

In some embodiments, the digital human replica system may receive input data from the human data acquisition system for both a target physical person and other persons with similar biomedical, social-demographical, occupational, and lifestyle characteristics for building, calibrating, and customizing the digital human simuli system for the target physical person to simulate the growing and aging, disease events, injury events, and their reactions to medicines and treatment plans.

In some embodiments, the digital human agent system may create a special digital human replica of actions, treatment plans, and decision makings of medical and healthcare professionals.

In some embodiments, the digital human agent system is configured to execute simulated medical, care, and health services as an intervention based on simulation in a digital human simuli model of the digital human simuli system, In some embodiments, the digital human stimuli and the digital human agent system may be integrated to perform model optimization to select and determine an optimal treatment or support plan to achieve an optimal health and medical outcome.

In some embodiments, the digital human digital data currency system awards digital currency for data contribution by the participating parties who interface with the digital human data acquisition system and wherein the data contribution results in improvement of performance of the digital human simuli system and the digital human agent system.

In some embodiments, the digital human replica system provides a representation of physical human bodies, and wherein the representation may include one or more of: 3D contour body model, multi-dimensional anatomical model, multi-dimensional data feature tensor, and spatiotemporal transformation of health and disease state.

In some embodiments, the representation further may include one or more of medical diagnosis and treatment; pharmaceutical use state quantity; diet, living and healthcare habits state quantity; environmental impact state quantity;

virtual detection monitoring and observation modeling; and a process of psychophysiological changes for a full life cycle.

In some embodiments, a digital human replica system may include a full retrospective system generated based on spatiotemporal data. In some embodiments, the spatiotemporal data may include: retrospective of life cycle, retrospective of life course and event process, or retrospective of disease and psychophysiological social environment impact events.

In some embodiments, the digital human replica system provides virtual representation, modeling, and visualization service for both participant users and non-participant users of the medical and healthcare service platform, wherein the non-participant users have similar biomedical, social-demographical, occupational, and lifestyle characteristics to the participant users, and wherein the digital human replica system uses the characteristics of the non-participant users to infer and interpolate missing data of the participant users.

In some embodiments, the digital human replica system is configured to: identify the participant users using customizable identity and biometric information, or receive feedback on physical human health or medical processes.

In some embodiments, the non-participant users are identified by de-identified information created by: age groups, gender, or biometric group characteristics, or a combination thereof.

In some embodiments, the digital human simuli system simulates based on current human health and biomedical conditions, includes: diagnosis and treatment: disease related, nutrition and health care, pharmacological responses of drug development, gene editing, health risk simulation, the human body's natural growth and aging process, disease occurrence, development, progression, lesion, termination or recovery, and its interaction with different drugs and therapeutic interventions, infection, symptoms, immunity, termination or recovery processes in public health and infectious diseases and their interactions with the environment and other digital human models, personal and family habits, food, physiotherapy, and health products, sports/Exercise health, pain chronic disease, rare disease simulation, development and recovery process of sports injuries and major trauma, mental health, organ transplant, pharmacogenomics simulation, or a combination thereof.

In some embodiments, the digital human simuli system may include an organ or part simulation subsystem that simulates a change process by using organs or parts of a constructed digital human replica.

In some embodiments, the digital human simuli system may include a simulation process dynamic visualization subsystem for dynamically visualizing changed data.

In some embodiments, the digital human agent system, through one or more deep neural network models, performs training and learning based on input data comprising: real-world doctors' treatment and prescription strategies, nursing and service strategies for nurses, therapists, research, experimentation, or development strategies for researchers, regulations and services for government agencies, wherein the digital human agent system generates digital human simuli models based on the input data, and wherein the digital human simuli models interact with a baseline digital human replica model.

In some embodiments, the digital human agent system creates deep neural network models of:

(a) doctors, nurses, or therapists to treat the digital human simuli and provide virtual instructions and services to physical persons on their healthcare and disease treatment process;

(b) researchers and experimental groups to conduct virtual tests and surveys on the digital human replica and the digital human simuli to conduct research and development of new medical devices, drugs, treatment plans, or general health and behavioral studies;

(c) health insurance providers that interact with the digital human replica about coverage and billing costs, insurance claims for ongoing treatments and services, and different treatment plans and insurance coverage and billing options;

(d) governing bodies, regulators, and digital security agencies to oversee, monitor and enforce critical health, medical, privacy protection, data security policy and regulations, freedom of information and disinformation suppression in virtual worlds;

(e) public health workers and platform users to provide related government services comprising medical material distribution, medical forms, and insurance claims; or (f) professionals who supervise scientific research and production services, and self-diagnosis services and volunteers who provide health diagnosis and treatment services to family members and family communities, wherein the digital human agent system undertakes medical treatment and care services, virtual simulation and modeling application.

In some embodiments, the present and past medical and health data may include: real time data, events data, and historical data and paper records.

In some embodiments, the data acquisition system may include an interface interacting with users and contributors of the medical and healthcare service platform to facilitate biomedical, healthcare, data inputs and labeling, and wherein the interface may include one or more of: an interface for regular individual participants, an interface for doctors and hospitals, an interface for companies and R&D groups, and an interface to interact with datasets and data feeds provided by public agencies.

In some embodiments, the interface may include: a wearable body health sensor interface, a digital human body multimodal data interface, a digital human body medical record conversion interface, or a combination thereof.

In some embodiments, the medical and health data are acquired from: wearable sensors, medical records, lab tests, or a combination thereof.

In some embodiments, the data acquisition system may be configured to: clean collected data; perform desensitization processing on collected data; perform data privacy protection processing on the collected data; or visualize the collected data.

In some embodiments, the medical and healthcare service platform constructs a spatial-temporal virtual world that simulates external factors related to human health, disease, conditions, and wherein the external factors may include one or more of: social activity, travel behavior, family environment, hospital, occupation, workplace, transportation, community, and city.

In some embodiments, the medical and healthcare service platform further may include an auxiliary and interactive system interfacing between the virtual world of digital humans and real-world personal healthcare and government public health management to perform one or more of:

auxiliary diagnosis and treatment, health care, nursing care, public health management, and smart device and robot interaction.

In some embodiments, the auxiliary diagnosis and treatment, health care, and nursing care may include: real-world medical diagnosis and treatment; emergency responses; diagnosis and treatment of rare diseases; offline personal health care; family daily care, emotional care, or psychological counseling; real-world offline community health management services; medical resource retrieval, distribution and sharing, equalization and fairness services; or a combination thereof.

In some embodiments, the public health management: conducts real-world government regulation, control disease, or infectious disease control; conducts national health education; prevents quack doctors or false medical information; or prevents and reduces major injury events with high accident rate and low rescue success rate.

In some embodiments, the medical and healthcare service platform may include a hybrid data warehouse system for storing the medical and health data, wherein the hybrid data warehouse system may include: a centralized data warehouse and a federated data warehouse, wherein the centralized data warehouse has an upload interface for users to upload their healthcare and medical data directly to the medical and healthcare service platform, and wherein the federated data warehouse has an application interface for the participating parties to share converted aggregate data and models from protected data sources within each party.

In some embodiments, the digital data currency system awards digital currency for one or more of: contributors based on entire data contribution and generation life cycles, contributions to early detection, tracking, and prevention of infectious diseases, success rate, and positive user feedback for healthcare worker agents, and successful applications and adoptions for research and discovery results from research and discovery agents.

Referring now to FIG. 1, a schematic structural diagram of an example medical healthcare service platform based on a human digital twin model is illustrated, according to various embodiments of the disclosure. In some embodiments, a human digital twin model-based medical and healthcare platform 101 may include: a digital human replica system 102, a digital human stimuli system 103, a digital human agent system 104, a digital human data acquisition system 105, and a digital human data currency system 106.

In some embodiments, the digital human replica system 102 may be configured to reconstruct a target human digital twin based on identity information, biometric information, and/or medical-related information. In some embodiments, the digital human replica system 102 may include: a digital human body data interface 1021 used to ingest current health and medical data of a system user, a digital human retrospective data interface 1022 that can take the inputs of historical medical and health data from health-monitoring device records, medical records, physical exam records, clinical trials and studies, a digital human model building system 1023 that reconstructs both the 4D model of a human body including the 3D dimension and temporal playback, but also any internal organs that have past or previous medical or health events, and a user access submodule 1024 that manages the access control for participating users.

In some embodiments, the digital human replica system 102 may determine a reconstruction category of a human digital twin model. In some embodiments, the reconstruction category may include one of the following: a participant member category, a non-participant member category. In some embodiments, the digital human replica system 102 may construct a human digital twin model based on the reconstruction category as determined.

In some embodiments, the digital human stimuli system 103 may be configured to perform a simulation process by using the human digital twin model. In some embodiments, the digital human stimuli system 103 may include: a human body simulation system 1031. In some embodiments, the human body simulation system 1031 may be configured to simulate a naturally occurring physiological process of a human body by using the human digital twin model. In some embodiments, the naturally occurring process may include one or more of the following processes: natural growth process, aging process, disease process, health state change process, and psychological change process.

In some embodiments, the digital human stimuli system 103 may further include: an external factor simulation system 1032. In some embodiments, the external factor simulation system 1032 may be configured to simulate the human digital twin model under the influence of different external factors. In some embodiments, the external factors may include one or more of the following factors: external environmental factors, occupational factors, dietary conditions, and habits, and sleeping conditions and habits.

In some embodiments, the digital human stimuli system 103 may also include: an organ and/or body part simulation submodule 1043. In some embodiments, the organ and/or body part simulation submodule 1043 may be configured to simulate the organs and/or parts of the human digital twin model.

In some embodiments, the digital human stimuli system 103 may further include: a simulation process dynamic visualization subsystem 1034. In some embodiments, the simulation process dynamic visualization subsystem 1034 may be configured to dynamically visualize the changed relevant data.

In some embodiments, the digital human stimuli system 103 may additionally include: a virtual environment reconstruction subsystem. In some embodiments, the virtual environment reconstruction subsystem may be configured to reconstruct a virtual environment required in the simulation process.

In some embodiments, the digital human agent system 104 may be configured to create representations of virtual medical and healthcare service professionals with specialties and functions. In some embodiments, the virtual medical and healthcare service professionals may be formed based on professional knowledge and capabilities, specialties, and experiences of physical medical and healthcare professionals and characteristics and specialties of non-medical and healthcare professionals or practitioners.

In some embodiments, the digital human agent system 104 may include: an artificial intelligence (AI) model subsystem 1041 that trains a deep neural network expert and natural language model with treatment and care decision-making and action histories of healthcare workers including doctors, nurses, therapists, family support members, social workers, and others, a model data interface 1042 that enables the cleaning, standardization, assisted automated, semi-automated or manual labeling process, and treatment or care performance data generation, a smart robot subsystem 1043 that can physically implement the selected treatment or care plan based on the optimization outcome with digital human simuli 102 system, and a digital human treatment subsystem 1044 that provides the selected medical, care, or exercise plans from the optimization outcome with digital human simuli 102 system to medical and healthcare professionals for their decision making, prescriptions, medical and/or health recommendations.

In some embodiments, the AI model may include one or more machine learning models. In some embodiments, the AI model may include a neural network, a convolutional neural network (CNN), a deep convolutional neural network (DCNN), a cascaded deep convolutional neural network, a simplified CNN, a shallow CNN, or a combination thereof.

As used herein, the term "convolutional neural network" or "CNN" refers to a deep feed-forward artificial neural network. Optionally, a convolutional neural network includes a plurality of convolutional layers, a plurality of up-sampling layers, and a plurality of down-sampling layers. For example, a respective one of the plurality of convolutional layers can process an image. An up-sampling layer and a down-sampling layer can change a scale of an input image to one corresponding to a certain convolutional layer. The output from the up-sampling layer or the down-sampling layer can then be processed by a convolutional layer of a corresponding scale. This enables the convolutional layer to add or extract a feature having a scale different from that of the input image. By pre-training, parameters include, but are not limited to, a convolutional kernel, a bias, and a weight of a convolutional layer of a convolutional neural network that can be tuned. Accordingly, the convolutional neural network can be used in various applications such as image recognition, image feature extraction, and image feature addition.

In some embodiments, the digital human data acquisition system 105 may be configured to collect identity information, biometric information, and/or medical-related information for reconstructing a human digital twin model. In some embodiments, the identity information may include one or more of: age, gender, name, ID number, race, community situation, and occupation. In some embodiments, the biometric information may include one or more of: data on height, weight, and physical signs. In some embodiments, the medical-related information may include one or more of: smoking history, drinking history, family medical history, exercise, diet, electronic medical record information, experimental data information, radiotherapy imaging information, pathological imaging information, genetic data, medication-related information, therapy and rehabilitation training-related information, follow-up record information, psychological assessment information.

In some embodiments, the digital human data acquisition system 105 may include one or more of: a wearable sensor interface 1051, a multimodal data interface 1052, and a digital medical record conversion interface (data processing subsystem) 1053.

In some embodiments, the digital human data acquisition system 105 may implement multiple data collection time stages. In some embodiments, the data collection time stages may include one or more of: pre-hospital stage, in-hospital stage, post-hospital stage, real-time collection stage, and timed collection stage.

In some embodiments, data collected in the pre-hospital stage may include one or more of following: target user race, community status, occupation, smoking history, drinking history, family medical history, physical activity, and diet.

In some embodiments, data collected in the in-hospital stages may include one or more of the following: unstructured electronic medical records, structured experimental data, radiotherapy imaging, pathological imaging and genetic data.

In some embodiments, data collected in the post-hospital stage may include one or more of the following: use of drugs, amount of drugs used, information related to rehabilitation training, information related to physical therapy, follow-up record information, and physical examination data.

In some embodiments, data collected in the real-time collection stage may include one or more of the following: data collected by using a wearable physical health sensor.

In some embodiments, data collected in the timed collection stage may include one or more of the following: data obtained by providing the user with a psychological health evaluation form at preset time intervals.

In some embodiments, the digital human data acquisition system 105 may further include a data processing subsystem 1053. In some embodiments, the data processing subsystem 1053 may: perform data cleaning processing on the collected data, perform desensitization processing on the collected data, and processing the collected data, perform data privacy protection processing, and/or visualize the collected data.

In some embodiments, the digital human data acquisition system 105 may also include a data interchange submodule for interacting with data contributors. In some embodiments, the digital human data acquisition system 105 may further include a data currency incentive submodule. In some embodiments, the data currency incentive submodule may be configured to provide a data provider with a virtual data currency reward based on the completeness and/or rarity of data.

In some embodiments, the medical and healthcare service platform 101 may collect identity information, biometric information, and medical-related information for reconstructing a human digital twin model. Based on the collected identity information, biometric information, and/or medical-related information, the digital human replica system 102 may reconstruct a target human digital twin body model. In some embodiments, the digital human stimuli system 103 may perform a simulation process using the reconstructed human digital twin model.

In some embodiments, the medical and healthcare service platform 101 may be implemented in hardware and/or software. In some embodiments, when implemented in hardware, it can be implemented as a distributed cluster composed of multiple servers or terminal devices or can be implemented as a single server or a single terminal device. In some embodiments, when implemented in software, it may be installed in the hardware devices mentioned above. For example, it can be implemented as multiple software or software modules for providing distributed services, or as a single software or software module.

In some embodiments, the medical and healthcare service platform may collect the identity information, biometric information, and medical information for reconstructing the human digital twin model, through the following steps:

At the first step, the medical and healthcare service platform may receive the identity information input from the target collection device, for example, through a wireless connection. The identity information includes one or more of the following information: age, gender, name, ID number, race, community situation, and occupation.

At the second step, the medical and healthcare service platform may collect biometric information by using a wearable health sensor interface. The biometric information may include one or more of the following: height, weight, and physical sign-related data. As an example, the sign-related data may include one or more of the following: heart rate, blood pressure, oxygen levels, and glucose levels.

At the third step, the medical and healthcare service platform may acquire the medical-related information by using the human digital twin multimodal data interface and the human digital twin body medical record conversion interface. In some embodiments, the multimodal data interface may be used to receive and store the uploaded data of multiple modalities such as radiotherapy images, pathology, and genes. In some embodiments, the medical record conversion interface may be used to convert text-based medical records or laboratory test data sheets into three-dimensional health dynamic data or labels of at least one part or organ. Specifically, the three-dimensional health dynamic data or labels may be used to reflect the three-dimensional image playback of the growth, health, and disease of the human body over time.

In some embodiments, the medical-related information may include one or more of the following information: smoking history, drinking history, family medical history, exercise, diet, electronic medical record information, experimental data information, radiotherapy imaging information, pathological imaging information, genetic data, medication information, therapy and rehabilitation training information, follow-up record information, and psychological assessment information.

In some embodiments, the collection process may be carried out at preset data collection time stages. In some embodiments, the preset data collection time stages may include one or more of the following: a pre-hospital stage, an in-hospital stage, a post-hospital stage, a real-time collection stage, and a timed collection stage. In some embodiments, the pre-hospital stage may include one or more of the following: the target user's race, community situation, occupation, smoking history, drinking history, family medical history, exercise status and diet. In some embodiments, the in-hospital stage may include one or more of the following: unstructured electronic medical records, structured experimental data, radiotherapy images, pathological images, and genetic data. In some embodiments, the post-hospital phase above may include one or more of the following: use of drugs, amount of drugs used, related to rehabilitation training information, physical therapy-related information, follow-up record information, and physical examination data. In some embodiments, the real-time collection stage may include one or more of the following: data collected by the wearable body health sensor. In some embodiments, the timed collection stage may include one or more of the following: data obtained by providing the user with a psychological and/or mental health evaluation form at preset time intervals.

In some embodiments, the collection process may include first cleaning the collected data. In some embodiments, data cleaning may include removal of missing, abnormal, and unreasonable data. In some embodiments, missing data (e.g., missing value data) may include data that has missing values exceeding a predetermined number of items or missing data for predetermined items. As an example, the number of preset items can be the third item, the preset items may be pre-specified items, and the collected data may include "Data A: 15, 89, 62, null, null, null, 63; Data B: 19, 90, 63, null, 55, 42", where "null" represents the replacement null value for missing data, then, according to the preset number of items, it can be determined that "data A" is the missing value data, if the pre-specified item is the first item, then it can be determined that "data B" does not belong to missing value data. If the pre-specified item is the fourth item, then it can be determined that "data B" belongs to missing value data.

In some embodiments, the collection process may include desensitizing or de-identify the collected data. Desensitization processing involves obscuring or removing valid data related to identity verification. As an example, the collected data may include "Data C: Name, 19, male, 231025199912126397, 15, 89, 62", wherein "Data C" includes name, age, gender, ID number, and other biometric information. The medical and healthcare service platform can determine the valid data "231025199912126397" in "Data C" involved in confirming the identity, and the executive body can hide (for example, not display) or delete the valid data, and obtain the processed "Data C: Name, 19, male, xxxxxxxxxxxxxxxxx, 15, 89, 62" or "Data C: Name, 19, male, null, 15, 89, 62."

In some embodiments, the collection process may additionally perform data privacy protection processing on the collected data. In the collection stage, methods such as anonymity technology and differential privacy can be used to resist attacks based on background knowledge caused by data integration and fusion; in the storage stage, encryption and auditing methods are used to ensure the confidentiality and integrity of data; In the sharing stage, based on the framework of federated learning and transfer learning, the model is updated by sharing some data weights, and the access rights of each object are strictly controlled, and the entire data process is closely tracked to ensure privacy and security.

In some embodiments, the collection process may perform data visualization processing on the collected data. In some embodiments, the visualization process may be a process of uniformly displaying the processed data after the data processing steps.

In some embodiments, the medical and healthcare service platform may include one or more interfaces for data interaction with the data contributors corresponding to the collected data. In some embodiments, data contributors can include individuals, family participants, doctors or hospitals, companies, and research and discovery (R&D) teams.

In some embodiments, the medical and healthcare service platform may include one or more interfaces for typical personal, household participants to establish data feeds directly with their health sensors, medical, healthcare, and laboratory testing platforms, as well as text- or paper-based upload interfaces for medical/drug usage records/logs.

In some embodiments, the medical and healthcare service platform may include one or more interfaces for physicians and hospitals for medical record exchange and for uploading user-consent or anonymized medical and laboratory test records, including real-time interfaces, electronic data transfer, image data upload, and text-based or paper-based document upload and processing. In some embodiments, the medical and healthcare service platform may include an interface for matching medical data with individual users of the platform with user consent.

In some embodiments, the medical and healthcare service platform may include one or more interfaces for companies and R&D teams to upload and exchange drug or medical testing/experimental records, medical survey data. In some embodiments, the medical and healthcare service platform may include one or more interfaces for potential contact or matching with individual users of the platform with their consent. In some embodiments, the medical and healthcare service platform may include one or more interfaces to interact with datasets and data feeds provided by public and community agencies, including open public data feeds and restricted datasets after data cleaning and anonymization.

In some embodiments, the medical and healthcare service platform may use identity information, biological feature information, and/or medical-related information to reconstruct a target human digital twin model.

In some embodiments, the medical and healthcare service platform may reconstruct the target human digital twin model through the following steps:

At the first step, the medical and healthcare service platform may obtain participant user-related information. In some embodiments, the medical and healthcare service platform may obtain the participant user-related information of the account to perform the reconstructing operation. In some embodiments, if the membership-related information is a null value, it indicates that the account is a non-member account. Conversely, if the membership-related information is not a null value, it indicates that the account is a member account.

At the second step, the medical and healthcare service platform may determine the category according to the member-related information. In some embodiments, the categories may include: participant user category or non-participant user category. As an example, if the participant user-related information is represented as a member account, the medical and healthcare service platform can determine that the reconstructing category of the human digital twin model is a member category, and if the user-related information is represented as a non-member account, the medical and healthcare service platform can determine that the category of this human digital twin model is a non-participant user account.

At the third step, if it is determined that the category is a participant user category, the medical and healthcare service platform may transmit the identity information, the biometric information, and the medical-related information to the module for reconstructing the target human digital twin model based on the category. If it is determined that the category is a non-participant user category, the medical and healthcare service platform may select a preset human digital twin model from the preset human digital twin model library as the target model based on the identity information and the biometric information and assign the collected data alien with the preset human digital twin model to the target human digital twin model.

In some embodiments, the medical and healthcare service platform may use the reconstructed target human digital twin model to perform simulation and modeling processes. In some embodiments, the medical and healthcare service platform may use the target human digital twin model to simulate the physiological process that occurs naturally in the human body. In some embodiments, the naturally occurring physiological process may include one or more of the following processes: natural growth process, aging process, disease process, health state change process, and psychological change process.

In some embodiments, the medical and healthcare service platform may use the target human digital twin model to perform external factor simulation for changes of the target human digital twin model under the influence of different external factors. In some embodiments, the external factors may include one or more of the following factors: external environmental factors, occupational factors, dietary conditions, and sleeping conditions and habits.

In some embodiments, the medical and healthcare service platform may simulate the change process by using the organs and/or parts of the target human digital twin model reconstructed above.

In some embodiments, when the simulation process is performed, the medical and healthcare service platform can dynamically display the changed relevant data in a dynamic and visual manner. In some embodiments, changed relevant data can be the data that has changed with the target human digital twin model when the model is reconstructed, and the dynamic visual display can be real-time monitoring of the changed data and forming the monitored data into a graph of real-time changes.

In some embodiments, before executing the simulation process, the medical and healthcare service platform may reconstruct a virtual environment required in the simulation process. In some embodiments, the virtual environment may be reconstructed according to the virtual environment reconstruction requirement information after receiving the transmitted virtual environment reconstruction requirement information.

In some embodiments, the medical and healthcare service platform may reconstruct a healthcare service robot terminal. In some embodiments, the medical and healthcare service platform may use an intelligent robot terminal to provide users with personalized, precise, and customizable health care services.

In some embodiments, the medical and healthcare service platform may invoke a trained model. In some embodiments, the invocation can be an in-demand invocation of the trained model, which is applied in the fields of career development, insurance industry, marriage, and family.

In some embodiments, the medical and healthcare service platform may include: a data collection unit, a human digital twin reconstruction unit, and a medical/healthcare simulation unit. In some embodiments, the data collection unit is configured to collect identity information, biometric information and medical-related information. In some embodiments, the human digital twin reconstruction unit is configured to reconstruct a target human digital twin model based on the identity information, the biometric information and/or the medical treatment information. In some embodiments, the medical/healthcare simulation unit is configured to perform a simulation process using the reconstructed human digital twin model.

In some embodiments, the data collection unit may be further configured to: receive identity information input for the target collection device; obtain biometric information by using the wearable body health sensor interface; and acquire medical-related information by using a multimodal data interface and a human digital medical record conversion interface.

In some embodiments, the identity information may include one or more of the following information: age, gender, name, ID number, race, community situation, and occupation. In some embodiments, the biometric information may include one or more of the following information: data related to height, weight, and physical signs. In some embodiments, the medical-related information may include one or more of the following information: smoking history, drinking history, family medical history, exercise, diet, electronic medical record information, experimental data information, radiotherapy imaging information, pathology image information, genetic data, medication-related information, therapy and rehabilitation training-related information, follow-up record information, and psychological assessment information.

In some embodiments, the medical and healthcare service platform may be configured to: perform data collection based on a preset data collection time stage. In some embodiments, the data collection time period may at least include: pre-hospital stage, in-hospital stage, post-hospital stage, real-time collection stage, and timed collection stage. In some embodiments, the pre-hospital stage may include one or more of the following: target user's race, community situation, occupation, smoking history, drinking history, family medical history, exercise, and diet. In some embodiments, the in-hospital phase may include one or more of the following: unstructured electronic medical records, structured experimental data, radiotherapy images, pathological images, and genetic data. In some embodiments, the post-hospital phase may include one or more of the following: use of drugs, amount of drugs used, information related to rehabilitation training, information related to physical therapy, follow-up record information, and physical examination data. In some embodiments, the real-time collection stage may include using a wearable physical health device or interface. In some embodiments, the timed collection stage may include: data obtained by providing the user with a psychological and/or mental health evaluation form at preset time intervals.

In some embodiments, the medical and healthcare service platform may be configured to: perform data cleaning processing on the collected data; perform desensitization processing on the collected data; perform data privacy processing on the collected data; and/or perform visualization processing on the collected data.

In some embodiments, the medical and healthcare service platform may be configured to perform data interaction with data contributors corresponding to the collected data.

In some embodiments, the medical and healthcare service platform may be configured to: determine the integrity and/or rarity of each piece of data in the collected data; and/or the rarity, and/or determine the data currency reward value of each piece of data in the collected data.

In some embodiments, the human digital twin reconstruction unit of the medical and healthcare platform may be further configured to: acquire participant member-related information; and/or determine a category based on the participant member-related information. In some embodiments, the categories may include: participant member category and/or non-participant member category. In some embodiments, the target human digital twin model may be reconstructed based on the identity information, the biometric information, the medical-related information, and/or the category after determining that the category is a member category.

In some embodiments, the medical/healthcare simulation unit of the medical and healthcare platform may be configured to: use the reconstructed human digital twin model to simulate the natural physiological behavior of the human body. In some embodiments, the naturally occurring physiological process may include one or more of the following processes: natural growth process, aging process, disease process, health state change process, and psychological change process.

In some embodiments, the medical/healthcare simulation unit of the medical and healthcare platform may be configured to: use the reconstructed human digital twin model to perform a simulation operation under the influence of different external factors. In some embodiments, the simulation may be influenced by external factors of the changes of the reconstructed human digital twin model. In some embodiments, the external factors may include one or more of the following factors: external environmental factors, occupational factors, eating conditions and habits, and sleeping conditions and habits.

In some embodiments, the medical/healthcare simulation unit may be further configured to simulate the changes of organs and/or parts over time based on the reconstructed human digital twin model.

In some embodiments, the medical and healthcare platform may be configured to dynamically visualize the changes of the relevant collected data. In some embodiments, the medical and healthcare platform may be further configured to: reconstruct a virtual environment requirement during the simulation process. In some embodiments, the medical and healthcare platform may be configured to reconstruct a personalized and precise health and medical service robot terminal.

In some embodiments, the medical and healthcare platform may be further configured for use in fields such as career development or insurance industry.

Figure 2:
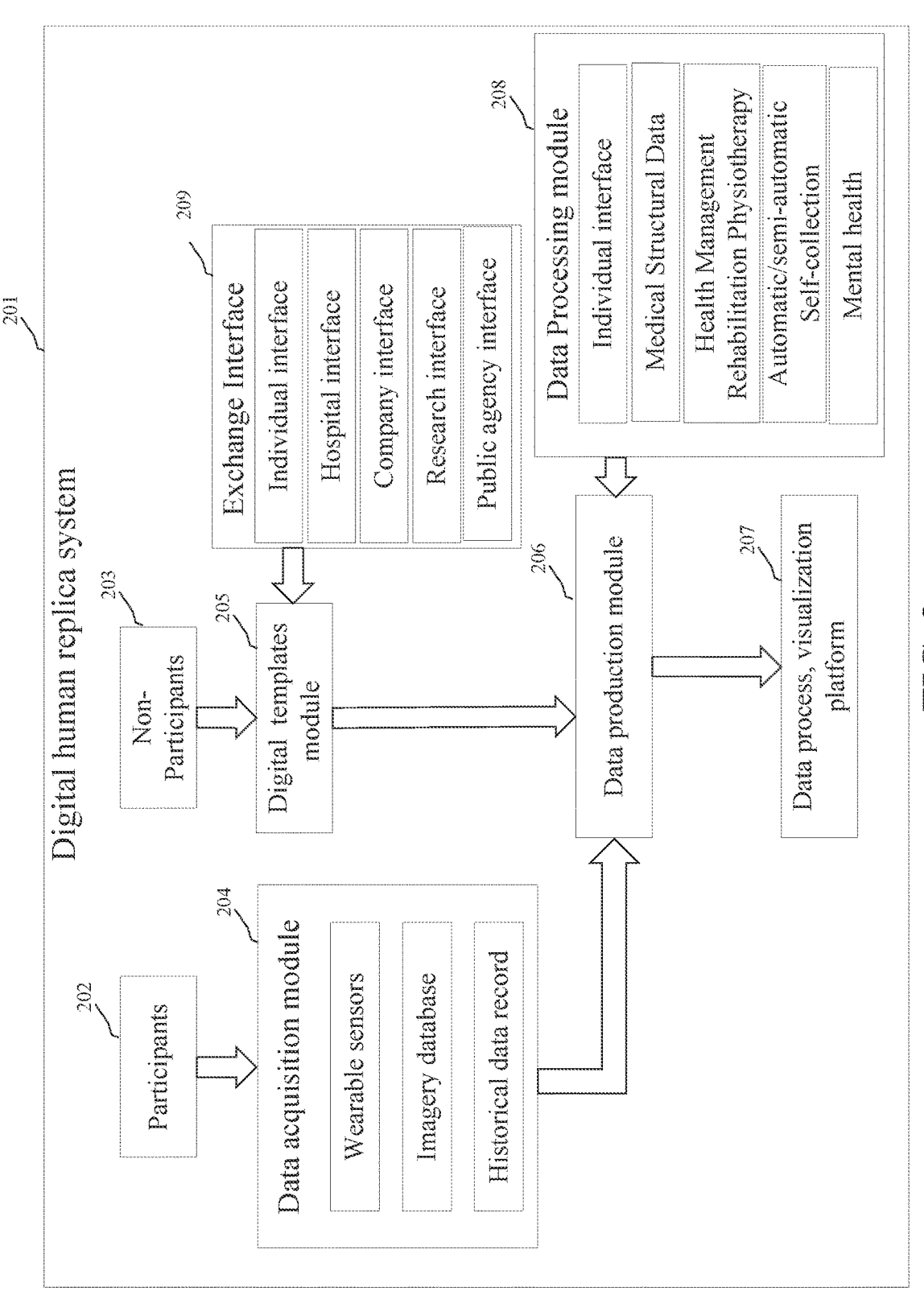
FIG. 2 illustrates an example process for digital human replica production for participant or non-participant users.

FIG. 2 is a schematic diagram of an application scenario of an example human digital replica system. The system works with both system participants 202 that registered with the platform and are active users of its services, as well as non-participants 203 whose anonymous data are obtained through contributors in the human digital twin data acquisition module 105 through related population studies, agency statistics and reports, research and clinical studies, anonymous user data from wearable or portable health-monitoring device service providers, and other primary or secondary healthcare datasets. Participant data are obtained through the participant data acquisition module 204, which can interact with wearable sensors, imagery databases, and other historical medical, health, and biological data records. Non-participant data will be collected through an exchange interface 209 to interact with different potential data sources such as individual volunteers, hospitals, technology companies, research institutes, and public agencies. The anonymous non-participant data will then be processed through the digital templates module 205 to reformat into a uniform format and data structure that can be used to conduct joint processing with participant data in the data production module 206.

In some embodiments, the data conversion module 208 may include the processing interface for specialized datasets such as individual data, the ingest and processing of medical structure data from different database systems, digital or written records from health management, rehabilitation, physiotherapy services, and mental health services, and automatically- or semi-automatically-collected self-reporting data. Finally, the processed data will be used for data processing, analytics, and visualization in the data processing module 207, where the acquired data will be further processed to feed into train and run inference on deep neural network and other machine learning/artificial intelligence models to create the analytics and visualization.

Figure 3:
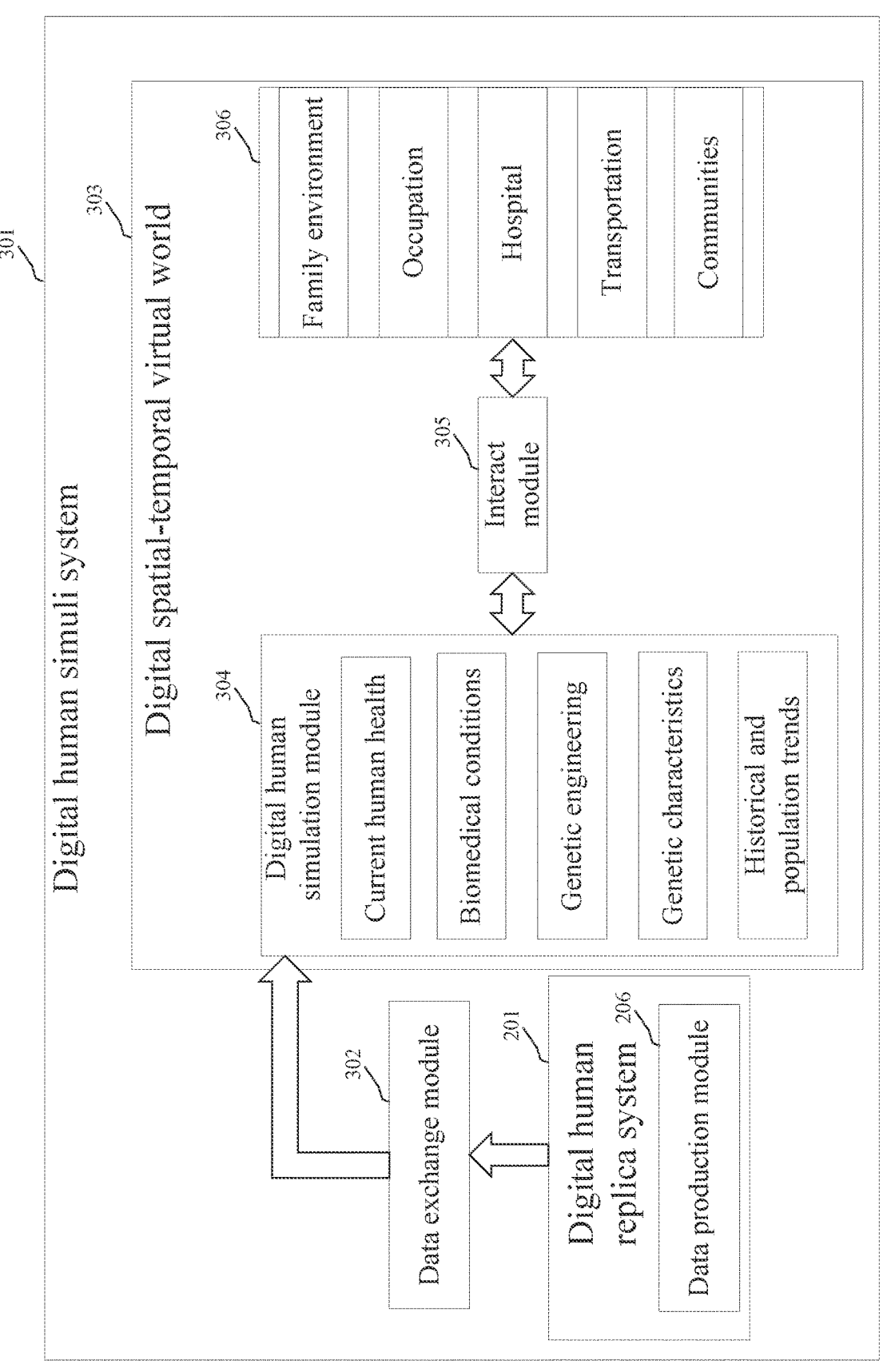
FIG. 3 illustrates an example process for providing data production in real world to a digital human simuli system in a virtual space.

FIG. 3 shows the system diagram of the digital human simuli system 301. The system takes the inputs from the data production module 206 of the digital human replica system 201 through a data exchange module 302 that converts the data from the digital human replica system into the baseline and historical data to be used in the simuli system. A spatial-temporal virtual world 303 will be established to build the digital human simulation module 304 that simulates human health, biomedical conditions, body growth or injuries, genetic characteristics, and the historical trends of the targeted physical human and his or her corresponding populations. The spatial-temporal virtual world 303 will also describe the characteristics related to the targeted physical human's living, working, and travel environment including family living conditions, occupation, hospital and medical environment, transportation environment, and the local community characteristics. An interaction module 305 will quantify the impact of the environment on different medical and health conditions of individuals.

Figure 4:
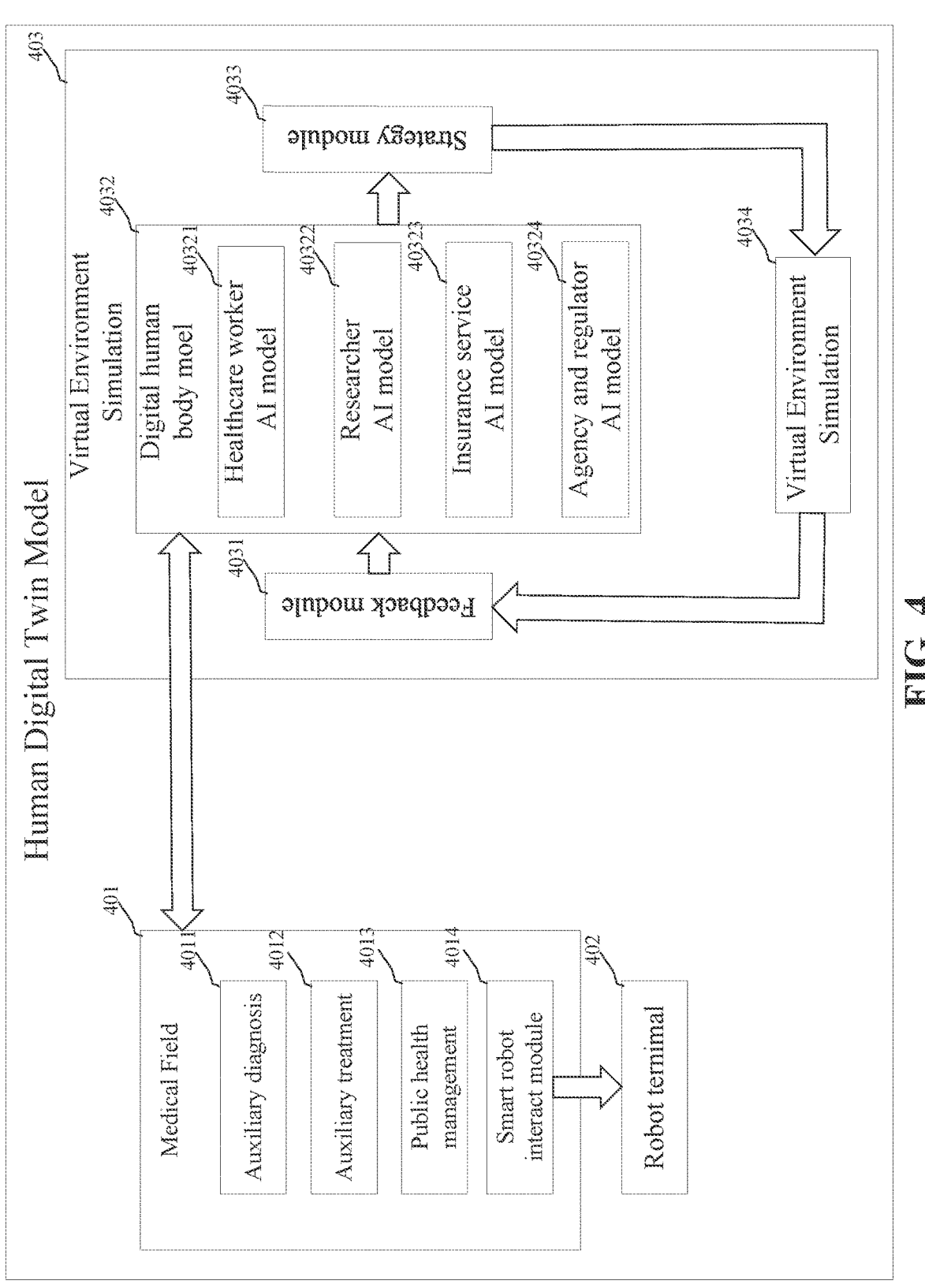
FIG. 4 illustrates an example process building digital twin human agent system in a virtual space to provide services in real world.

Referring now to FIG. 4, an example process building digital twin human agent system in a virtual space to provide services in the real world, according to various embodiments of the present disclosure. In some embodiments, when the human digital twin model is applied to the call of the intelligent robot in the medical field 401, it can realize agent-based physical world application systems, including auxiliary diagnosis 4011, auxiliary treatment 4012, public health management 4013, and interaction with the smart robot interface 4014, for example, by engaging a robot terminal 402.

In some embodiments, when the human digital twin model and the digital spatial-temporal virtual world 403 are reconstructed, the human digital twin model can be trained to obtain a digital human agent module, including artificial intelligence models for healthcare workers 40321, artificial intelligence models for researchers 40322, artificial intelligence models for insurance services 40323, and institutions and artificial intelligence models for regulators 40324. At the same time, the training process also includes feedback module 4031 and strategy module 4033, mediated by a virtual environment simulation system 4034.

Figure 5:
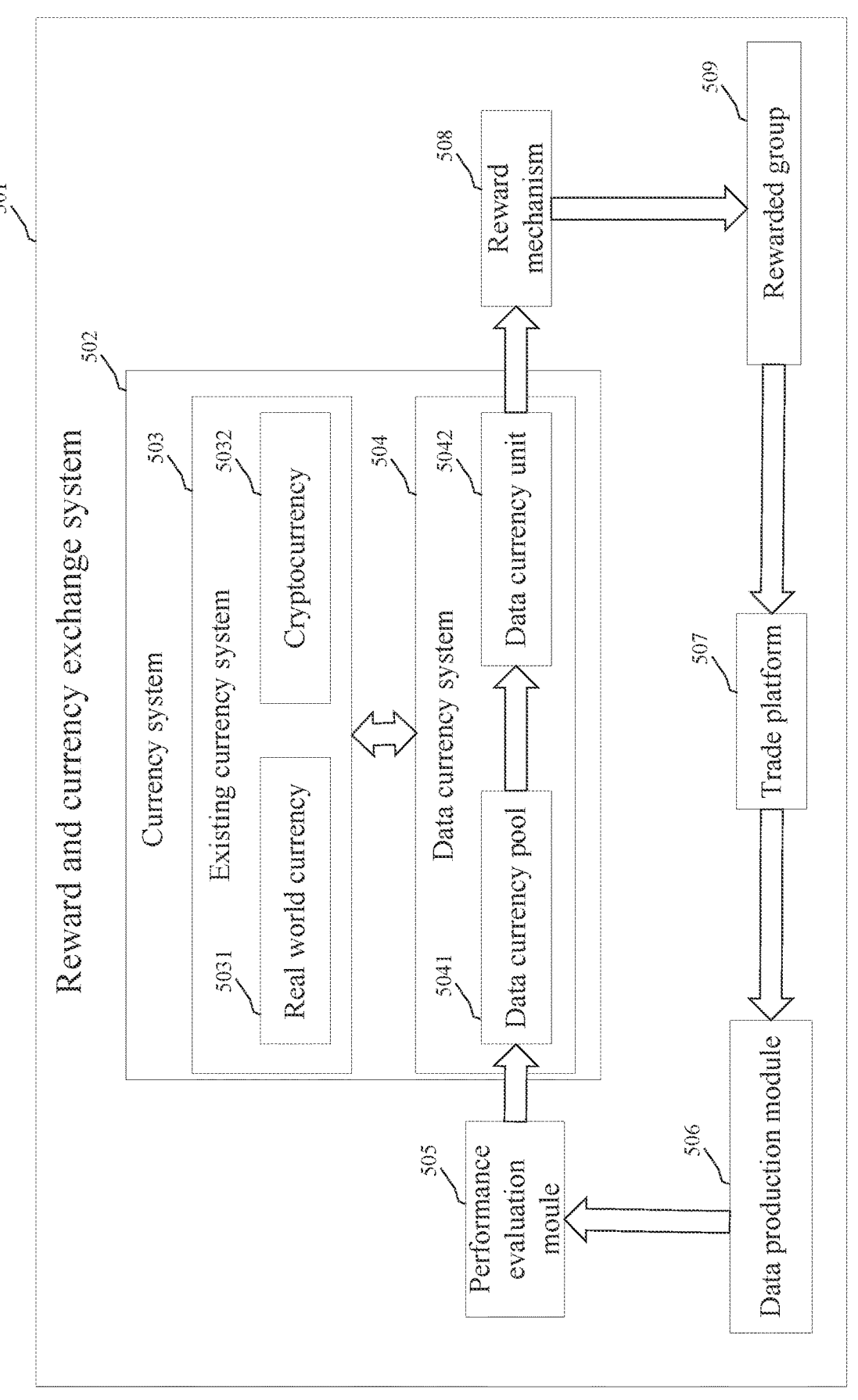
FIG. 5 illustrates an example process for trade and award operation of digital data currency.

FIG. 5 shows an example digital human data reward and currency exchange system 501 used to motivate and support the contribution to the digital human data acquisition system 105. The core system is the currency system 502 that consists of existing currency systems 503 with real-world currency 5031, cryptocurrency 5032, and the data currency system 504 built for digital human platform with its core module the data currency pool 5041 and data currency unit valuation 5042 determined by the quality and performance of the data products or applications from the data production module 506. The produced data will be fed into the performance evaluation module 505 to determine how much performance improvement of the AI models is gained with the new data. The performance improvement will be used to establish the size of the new data currency pool and the unit valuation. The trade platform 507 allows the trading of the digital human related datasets and feed into the data production module 506. The reward mechanism 508 will determine the distribution of new data currency to all contributors of the data production in the rewarded group 509 where the allocation will be distributed among data sources, data cleaners, data labelers, data modelers, data evaluators, computing and platform providers, and other contributors to the production.

Figure 6:
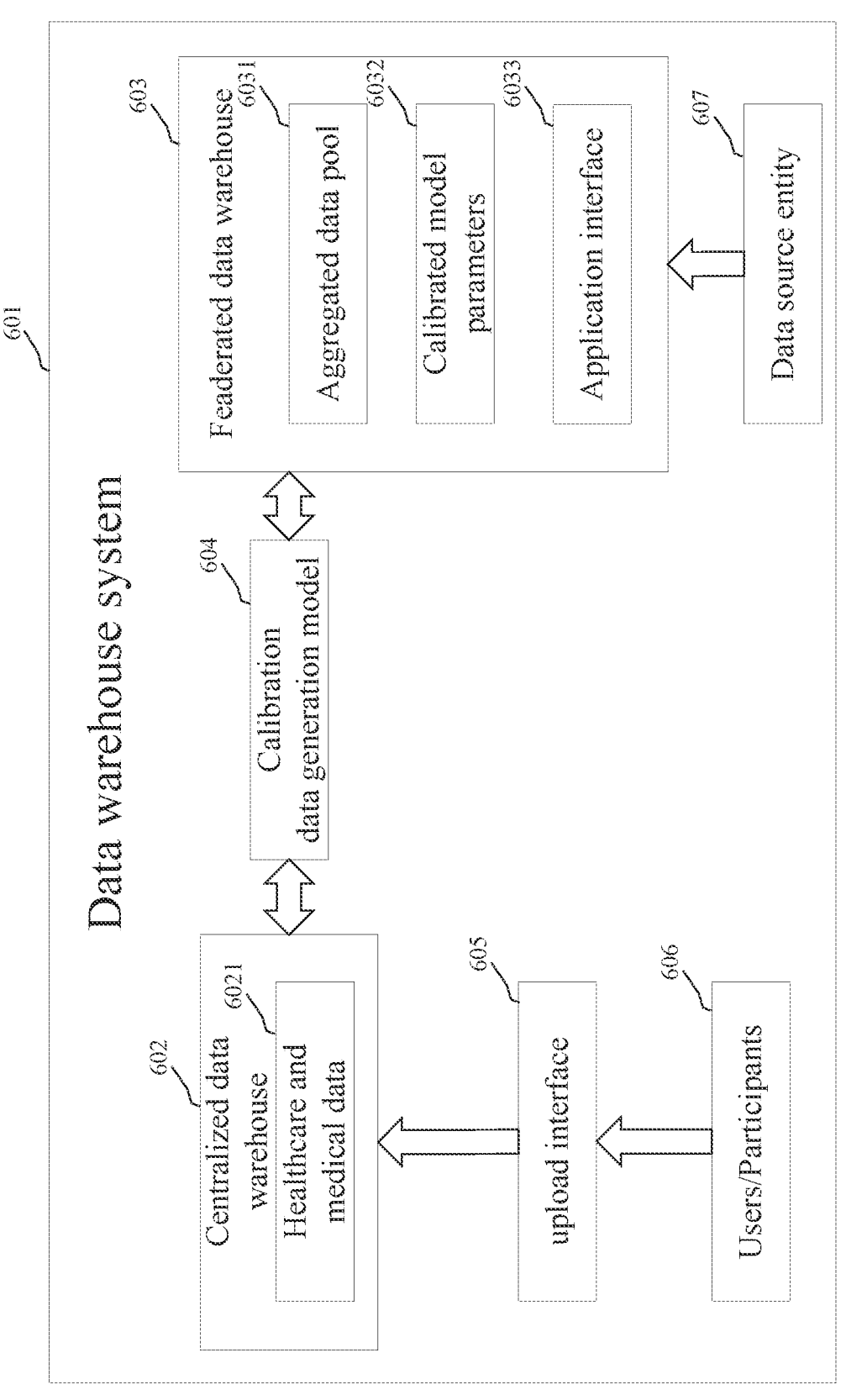
FIG. 6 illustrates an example structure of a data warehouse system for storing and processing collected data.

FIG. 6 shows an example integrated data warehouse system 601 for the human digital twin system. The data warehouse is constructed to accommodate different ways of data sharing with or without restrictions to the original datasets. When the original data is shareable, users and participants 606 can share through an uploading interface 605 directly to a centralized data warehouse 602. The data warehouse 602, especially the healthcare and medical data 6021, will then be converted into calibration data by the calibration data generation model 604 which can be an automated or semi-automated data processing and labeling model. The outcome will be used to calibrate the AI models such as the deep neural network model in the main modules of the human digital twin platform. However, if the original data is not allowed to leave the local networks of data source entities 607 such as agencies, hospitals, research institutes and other entities, the federated data warehouse structure will be used. The calibration data generation model 604 and the corresponding AI model calibration module will be distributed through application interface 6033 to local servers behind firewalls of those restricted entities. The calibrated model parameters 6032 will then be fed back to the main analytic servers of the digital human platform to be integrated with the calibrated model parameters from the centralize data warehouse. Furthermore, if allowed, aggregated data pool 6031 can be build to transmit aggregated measures, such as generate demographical, medical, and health record statistics, can also be shared with the calibration data general model to assist the integration of different model parameters from the two different warehouse architectures.

Figure 7:
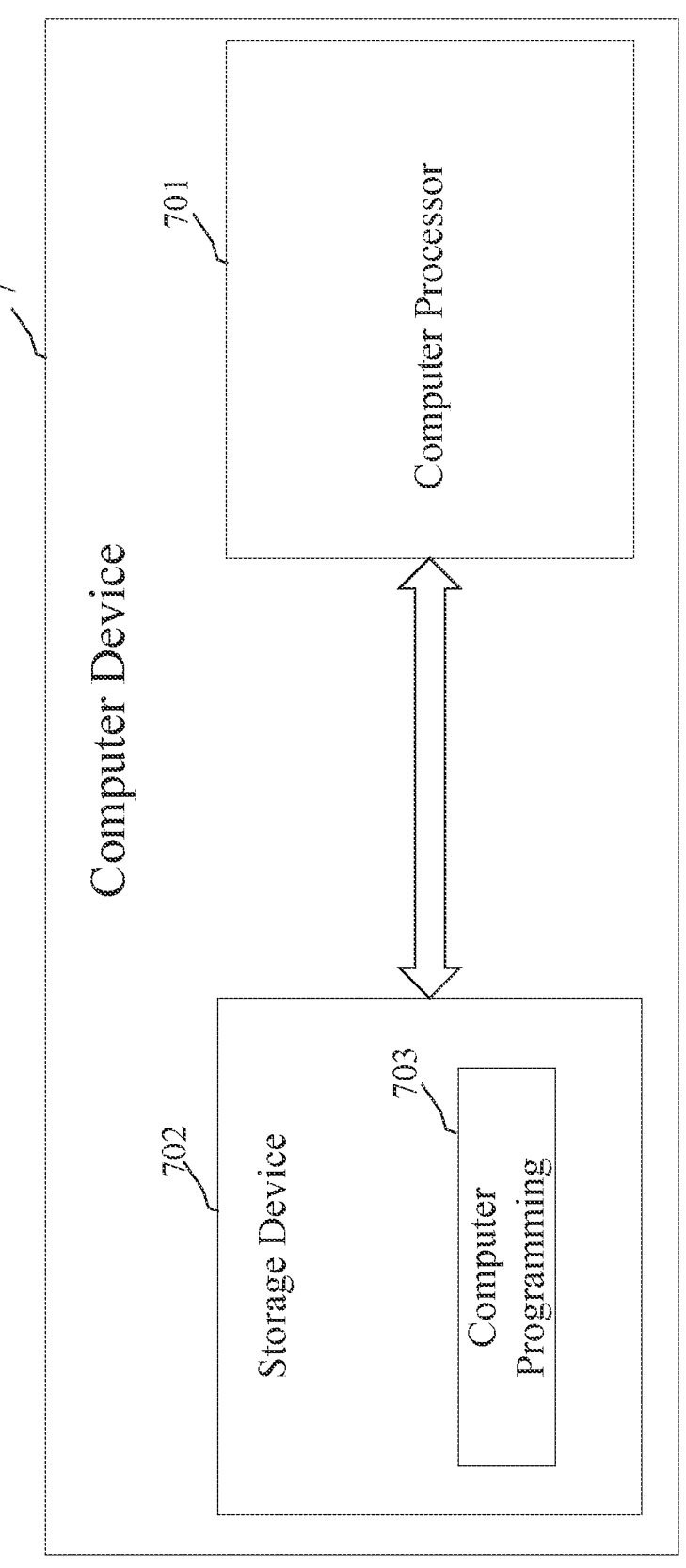
FIG. 7 illustrates an example computing device suitable for implementing the disclosed medical and healthcare service platform.

Referring now to FIG. 7, an example computing device suitable for implementing the disclosed medical and healthcare service platform is illustrated, according to various embodiments of this disclosure. As shown in FIG. 7, computer device 7 of this embodiment includes a processing unit 701, a storage unit 702, and a computer program 703 stored in the storage unit 702 and executable on the processing unit 701. When processing unit 701 executes computer program 703, the steps in each of the foregoing method embodiments are implemented. Alternatively, when processing unit 701 executes the computer program 703, the functions of the modules/units in the foregoing device embodiments are implemented.

The computer program 703 can be divided into one or more modules/units, which are stored in storage unit 702 and executed by processing unit 701 to complete the present disclosure. One or more modules/units can be a series of computer program instruction segments capable of performing specific functions, and the instruction segments are used to describe the execution process of computer program 703 in the computer device 7.

Computer device 7 can be a desktop computer, a laptop, a palmtop computer, a cloud server, and other computer devices. Computer device 7 can include, but is not limited to, processing unit 701 and storage unit 702. Those skilled in the art should understand that FIG. 7 is only an example of the computer device 7 and does not constitute a limitation to the computer device 7 and may include components than those shown, or combine some components, or different components for example, a computer device may also include input and output devices, network access devices, and buses.

The processing unit 701 may be a Central Processing Unit (CPU), or other general-purpose processing units, Digital Signal Processors (DSP), Application Specific Integrated Circuit (ASIC), Field-Programmable Gate Array (FPGA) or other programmable logic devices, discrete gate or transistor logic devices, discrete hardware components. A general-purpose processing unit may be a micro processing unit, or the processing unit may be any conventional processing unit or the like.

The storage unit 702 may be an internal storage unit of the computer device 7, for example, a hard disk or a storage unit of the computer device 7. The storage unit 702 can also be an external storage device of computer device 7, for example, a pluggable hard disk, a Smart Media Card (SMC), a Secure Digital (SD) card, a flash memory card (Flash Card). Further, the storage unit 702 can also include both an internal storage unit of the computer device 7 and an external storage device. Storage unit 702 is used to store computer programs and other programs and data required by the computer device. Storage unit 702 can also be used to temporarily store data that has been or will be output.

Those skilled in the art should clearly understand that, for the convenience and simplicity of description, only the division of the functional units and modules is used as an example. Module completion means dividing the internal structure of the device into different functional units or modules to complete all or part of the functions described above. Each functional unit and module in the embodiment may be integrated into one processing unit, or each unit may exist physically alone, or two or more units may be integrated in one unit, and the integrated units may adopt hardware. It can also be realized in the form of software functional units. In addition, the specific names of the functional units and modules are only for the convenience of distinguishing them from each other and are not used to limit the protection scope of the present application. For the specific working processes of the units and modules in the system, reference may be made to the corresponding processes in the foregoing method embodiments, which will not be repeated here.

In the foregoing embodiments, the description of each embodiment has its own emphasis. For parts that are not described or described in detail in a certain embodiment, reference may be made to the relevant descriptions of other embodiments.

Those of ordinary skill in the art can realize that the units and algorithm steps of each example described in conjunction with the embodiments disclosed herein can be implemented in electronic hardware, or a combination of computer software and electronic hardware. Whether these functions are performed in hardware or software depends on the specific application and design constraints of the technical solution. Skilled artisans may implement the described functionality using different methods for each application, but such implementations should not be considered beyond the scope of this disclosure.

In the embodiments provided in this disclosure, it should be understood that the disclosed apparatus/computer device and method can be implemented in other ways. For example, the embodiments of the apparatus/computer device described above are merely illustrative, and the division of modules or units is only a logical function division. In actual implementation, there may be other division methods, multiple units or components can be combined or integrated into another system, some features can be ignored or not executed. In addition, the coupling or direct coupling or communication connection between the shown or discussed elements can be an indirect coupling or communication connection between some interfaces, apparatuses, or units, which can be electrical, mechanical or other forms.

Units described as separate components may or may not be physically separated, and components shown as units may or may not be physical units, that is, may be in one place, or may be distributed to multiple network units. Some or all the units may be selected according to actual needs to achieve the purpose of the solution in this embodiment.

In addition, each functional unit in each embodiment of the present disclosure may be integrated into one processing unit, or each unit may exist physically alone, or two or more units may be integrated into one unit. The integrated units may be implemented in the form of hardware or may be implemented in the form of software functional units.

The integrated modules/units, if implemented in the form of software functional units and sold or used as stand-alone products, may be stored in a computer-readable storage medium. Based on this understanding, the present disclosure can implement all or part of the processes in the methods of the above embodiments and can also be completed by instructing relevant hardware through a computer program. The computer program can be stored in a computer-readable storage medium, and the computer program can be processed. When the device is executed, the steps of the foregoing method embodiments may be implemented. A computer program may include computer program code, which may be in source code form, object code form, executable file, or some intermediate form, and the like. Computer-readable media may include: any entity or device capable of carrying computer program codes, recording media, USB flash drives, removable hard disks, magnetic disks, optical discs, computer memory, Read-Only Memory (ROM), Random Access Memory (RAM), electric carrier signal, telecommunication signal, and software distribution medium. It should be noted that the content contained in computer-readable media may be modified as appropriate in accordance with the requirements of legislation and patent practice in the jurisdiction. For example, in some jurisdictions, according to legislation and patent practice, computer-readable media may not include electrical carrier signals and telecommunication signals.

Additional Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The terms "memory," "memory device," "computer-readable storage medium," "data store," "data storage facility," and the like each refer to a non-transitory device on which computer-readable data, programming instructions or both are stored. Except where specifically stated otherwise, the terms "memory," "memory device," "computer-readable storage medium," "data store," "data storage facility," and the like are intended to include single device embodiments, embodiments in which multiple memory devices together or collectively store a set of data or instructions, as well as individual sectors within such devices.

The terms "processor" and "processing device" refer to a hardware component of an electronic device that is configured to execute programming instructions. Except where specifically stated otherwise, the singular term "processor" or "processing device" is intended to include both single-processing device embodiments and embodiments in which multiple processing devices together or collectively perform a process.

The terms "instructions" and "programs" may be used interchangeably herein. The instructions may be stored in object code format for direct processing by the processor, or in any other computing device language, including scripts or collections of independent source code modules that are interpreted on demand or compiled in advance. Functions, methods, and routines of the instructions are explained in more detail below. The instructions may be any set of instructions to be executed directly (such as machine code) or indirectly (such as scripts) by the processor. For example, the instructions may be stored as computing device code on the computing device-readable medium.

In addition, the terms "unit," "-er," "-or," and "module" described in the specification mean units for processing at least one function and operation, and can be implemented by hardware components or software components and combinations thereof.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

Aspects of the present disclosure are described herein with reference to flowchart illustrations and/or block diagrams of methods, apparatus (systems), and computer program products according to embodiments of the invention. In some embodiments, the flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Unless specifically stated otherwise, it is appreciated that throughout the disclosure, descriptions utilizing terms such as "obtaining," "performing," "receiving," "computing," "associating," "assigning," "traversing," "calculating," "determining," "identifying," "transforming," "ranking," "providing," "transmitting," or the like, refer to the action and processes of a computer system, or similar electronic computing device, that manipulates and transforms data represented as physical (or electronic) quantities within the computer system memories or registers or other such information storage, transmission or display devices.

As used herein, the term "logistic regression" is a regression model for binary data from statistics where the logit of the probability that the dependent variable is equal to one is modeled as a linear function of the dependent variables.

As used herein, the term "neural network" is a machine learning model for classification or regression consisting of multiple layers of linear transformations followed by element-wise nonlinearities typically trained via stochastic gradient descent and back-propagation.

The term "machine learning," as used herein, refers to a computer algorithm used to extract useful information from a database by building probabilistic models in an automated way.

The term "regression tree," as used herein, refers to a decision tree that predicts values of continuous variables.

It will be understood that, although the terms "first," "second," etc., may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A medical and healthcare service platform, wherein the medical and healthcare service platform is supported by a digital data currency system and provides medical and healthcare data processing, analyzing, and predicting based on a digital human system by integrating participating parties comprising individual persons, researchers, healthcare providers, and regulatory and public sectors, the medical and healthcare service platform comprising:

a digital human replica system that constructs a digital human replica to provide virtual representation, modeling, and visualization services based on present and past medical and health data of physical persons;

a digital human simuli system that constructs a digital human simuli to provide virtual simulation and modeling of future health and physiological evolution of a physical person based on the present and past medical and health data;

a digital human agent system that represents virtual medical and health service professionals with specialties and functions, wherein the virtual medical and healthcare service professionals are formed based on professional knowledge and capabilities, specialties, and experiences of physical medical and healthcare professionals and characteristics and specialties of non-medical and healthcare professionals or practitioners; and a digital human data acquisition system that collects biometric identification and medical-related data, wherein the digital data currency system awards data sharing and contributions in a full ecosystem of data generation comprising data processing, data cleaning and denoising, data encryption and anonymization, data labeling and calibration, and data analytics, data contributions related to medical and healthcare services; and services provided by medical and healthcare professionals from clinical practices, drug companies from laboratories or clinical trial data, and academic researchers from research work, wherein the digital human replica system receives input data from the human data acquisition system for both a target physical person and other persons with similar biomedical, social-demographical, occupational, and lifestyle characteristics for building, calibrating, and customizing the digital human simuli system for the target physical person to simulate the growing and aging, disease events, injury events, and their reactions to medicines and treatment plans, wherein the digital human agent system creates a special digital human replica of actions, treatment plans, and decision makings of medical and healthcare professionals, the digital human agent system configured to execute simulated medical, care, and health services as an intervention based on simulation in a digital human simuli model of the digital human simuli system, wherein the digital human stimuli and the digital human agent system are integrated to perform model optimization to select and determine an optimal treatment or support plan to achieve an optimal health and medical outcome, wherein the digital human digital data currency system awards digital currency for data contribution by the participating parties who interface with the digital human data acquisition system and wherein the data contribution results in improvement of performance of the digital human simuli system and the digital human agent system, wherein the digital data currency system awards digital currency for one or more of: contributors based on entire data contribution and generation life cycles, contributions to early detection, tracking, and prevention of infectious diseases, success rate, and positive user feedback for healthcare worker agents, and successful applications and adoptions for research and discovery results from research and discovery agents, and wherein the data acquisition system is configured to:
a) clean collected data;
b) perform desensitization processing on collected data;
c) perform data privacy protection processing on the collected data; and,
d) visualize the collected data, wherein data privacy protection processing on the collected data supports updating the digital human simuli model based on federated learning and transfer learning by sharing selected data weights, wherein such updates are applied under controlled access rights and tracked processes to preserve the integrity and performance of the digital human simuli model.

2. The medical and healthcare service platform of claim 1, wherein the digital human replica system provides a representation of physical human bodies, and wherein the representation comprises one or more of: 3D contour body model, multi-dimensional anatomical model, multi-dimensional data feature tensor, and spatiotemporal transformation of health and disease state.

3. The medical and healthcare service platform of claim 2, wherein the representation further comprises one or more of medical diagnosis and treatment; pharmaceutical use state quantity; diet, living and healthcare habits state quantity; environmental impact state quantity; virtual detection monitoring and observation modeling; and a process of psychophysiological changes for a full life cycle.

4. The medical and healthcare service platform of claim 1, wherein the digital human replica system comprises a full retrospective system generated based on spatiotemporal data, and wherein the spatiotemporal data comprises: retrospective of life cycle, retrospective of life course and event process, or retrospective of disease and psychophysiological social environment impact events.

5. The medical and healthcare service platform of claim 1, wherein the digital human replica system provides virtual representation, modeling, and visualization service for both participant users and non-participant users of the medical and healthcare service platform, wherein the non-participant users have similar biomedical, social-demographical, occupational, and lifestyle characteristics to the participant users, and wherein the digital human replica system uses the characteristics of the non-participant users to infer and interpolate missing data of the participant users.

6. The medical and healthcare service platform of claim 5, wherein the digital human replica system is configured to: identify the participant users using customizable identity and biometric information, or receive feedback on physical human health or medical processes.

7. The medical and healthcare service platform of claim 5, wherein the non-participant users are identified by de-identified information created by: age groups, gender, or biometric group characteristics.

8. The medical and healthcare service platform of claim 1, wherein the digital human simuli system comprises an organ or part simulation subsystem that simulates a change process by using organs or parts of a constructed digital human replica.

9. The medical and healthcare service platform of claim 1, wherein the digital human simuli system comprises a simulation process dynamic visualization subsystem for dynamically visualizing changed data.

10. The medical and healthcare service platform of claim 1, wherein the digital human agent system, through one or more deep neural network models, performs training and learning based on input data comprising: real-world doctors' treatment and prescription strategies, nursing and service strategies for nurses, therapists, research, experimentation, or development strategies for researchers, regulations and services for government agencies, wherein the digital human agent system generates digital human simuli models based on the input data, and wherein the digital human simuli models interact with a baseline digital human replica model.

11. The medical and healthcare service platform of claim 10, wherein the digital human agent system creates deep neural network models of:
(a) doctors, nurses, or therapists to treat the digital human simuli and provide virtual instructions and services to physical persons on their healthcare and disease treatment process;
(b) researchers and experimental groups to conduct virtual tests and surveys on the digital human replica and the digital human simuli to conduct research and development of new medical devices, drugs, treatment plans, or general health and behavioral studies;
(c) health insurance providers that interact with the digital human replica about coverage and billing costs, insurance claims for ongoing treatments and services, and different treatment plans and insurance coverage and billing options;
(d) governing bodies, regulators, and digital security agencies to oversee, monitor and enforce critical health, medical, privacy protection, data security policy and regulations, freedom of information and disinformation suppression in virtual worlds;
(e) public health workers and platform users to provide related government services comprising medical material distribution, medical forms, and insurance claims; or
(f) professionals who supervise scientific research and production services, and self-diagnosis services and volunteers who provide health diagnosis and treatment services to family members and family communities, wherein the digital human agent system undertakes medical treatment and care services, virtual simulation and modeling application.

12. The medical and healthcare service platform of claim 1, wherein the present and past medical and health data comprises: real time data, events data, and historical data and paper records.

13. The medical and healthcare service platform of claim 1, wherein the data acquisition system comprises an interface interacting with users and contributors of the medical and healthcare service platform to facilitate biomedical, healthcare, data inputs and labeling, and wherein the interface comprises one or more of: an interface for regular individual participants, an interface for doctors and hospitals, an interface for companies and R&D groups, and an interface to interact with datasets and data feeds provided by public agencies.

14. The medical and healthcare service platform of claim 13, wherein the interface comprises: a wearable body health sensor interface, a digital human body multimodal data interface, or a digital human body medical record conversion interface.

15. The medical and healthcare service platform of claim 14, wherein the medical and health data are acquired from: wearable sensors, medical records, or lab tests.

16. The medical and healthcare service platform of claim 1, wherein the medical and healthcare service platform constructs a spatial-temporal virtual world that simulates external factors related to human health, disease, conditions, and wherein the external factors comprise one or more of: social activity, travel behavior, family environment, hospital, occupation, workplace, transportation, community, and city.

17. The medical and healthcare service platform of claim 16, comprising an auxiliary and interactive system interfacing between the virtual world of digital humans and real-world personal healthcare and government public health management to perform one or more of: auxiliary diagnosis and treatment, health care, nursing care, public health management, and smart device and robot interaction, wherein the auxiliary diagnosis and treatment, health care, and nursing care comprises: real-world medical diagnosis and treatment; emergency responses; diagnosis and treatment of rare diseases; offline personal health care; family daily care, emotional care, or psychological counseling; real-world offline community health management services; or medical resource retrieval, distribution and sharing, equalization and fairness services, and wherein the public health management: conducts real-world government regulation, control disease, or infectious disease control; conducts national health education; prevents quack doctors or false medical information; or prevents and reduces major injury events with high accident rate and low rescue success rate.

18. The medical and healthcare service platform of claim 1, comprising a hybrid data warehouse system for storing the medical and health data, wherein the hybrid data warehouse system comprises: a centralized data warehouse and a federated data warehouse, wherein the centralized data warehouse has an upload interface for users to upload their healthcare and medical data directly to the medical and healthcare service platform, and wherein the federated data warehouse has an application interface for the participating parties to share converted aggregate data and models from protected data sources within each party.

* * * * *